United States Patent [19]

Thomas

[11] 4,179,051
[45] Dec. 18, 1979

[54] ONE-PIECE CHECK VALVE FOR USE IN A FLUID DISPENSER

[75] Inventor: Michael D. Thomas, Arab, Ala.

[73] Assignee: Ryder International Corporation, Barrington, Ill.

[21] Appl. No.: 820,638

[22] Filed: Aug. 1, 1977

[51] Int. Cl.² ............................ B65D 39/00; F16K 15/14
[52] U.S. Cl. .................................. 222/494; 137/454.2; 137/855
[58] Field of Search ........................... 222/491–497; 137/843, 852–859, 527, 527.4, 454.2, 454.4

[56] References Cited
U.S. PATENT DOCUMENTS

| 1,992,067 | 2/1935 | Gunn | 222/494 X |
| 2,012,950 | 9/1935 | Block | 222/494 |
| 2,105,695 | 1/1938 | Lateur | 222/494 |
| 3,128,785 | 4/1964 | Krummel | 137/527 |
| 3,360,169 | 12/1967 | Susuki et al. | 222/494 X |
| 3,365,138 | 1/1968 | Green | 222/494 X |
| 3,814,124 | 6/1974 | Bell | 137/855 |

*Primary Examiner*—Francis J. Bartuska
*Attorney, Agent, or Firm*—Trexler, Wolters, Bushnell & Fosse, Ltd.

[57] ABSTRACT

There is disclosed herein a one-piece check valve for use in an applicator tip for fluid substances, or the like, comprises a reed portion and a valve seat portion and an interconnecting integral hinge section, permitting the respective portions to be folded over and engaged in superposed relation. Further, the valve includes a flange segment also preferably formed in halves adjacent the inlet sections of the reed and seat portions. The respective portions are molded as an integral unit, and upon assembly, the respective reed and valve seat portions are folded over at the hinge portion so that the reed portion seats on the seat provided by the valve seat portion, and the flange segment halves abut to form a valve inlet and an abutment shoulder extending outwardly of the inlet for engaging complimentary retaining shoulders, flanges or the like of the applicator or other fluid carrying device. As such, fluid entering the applicator will pass through the check valve, and can exit the valve quite easily; however, any back-flow through the applicator is prevented by the engagement of the reed on the shoulder portion.

7 Claims, 4 Drawing Figures

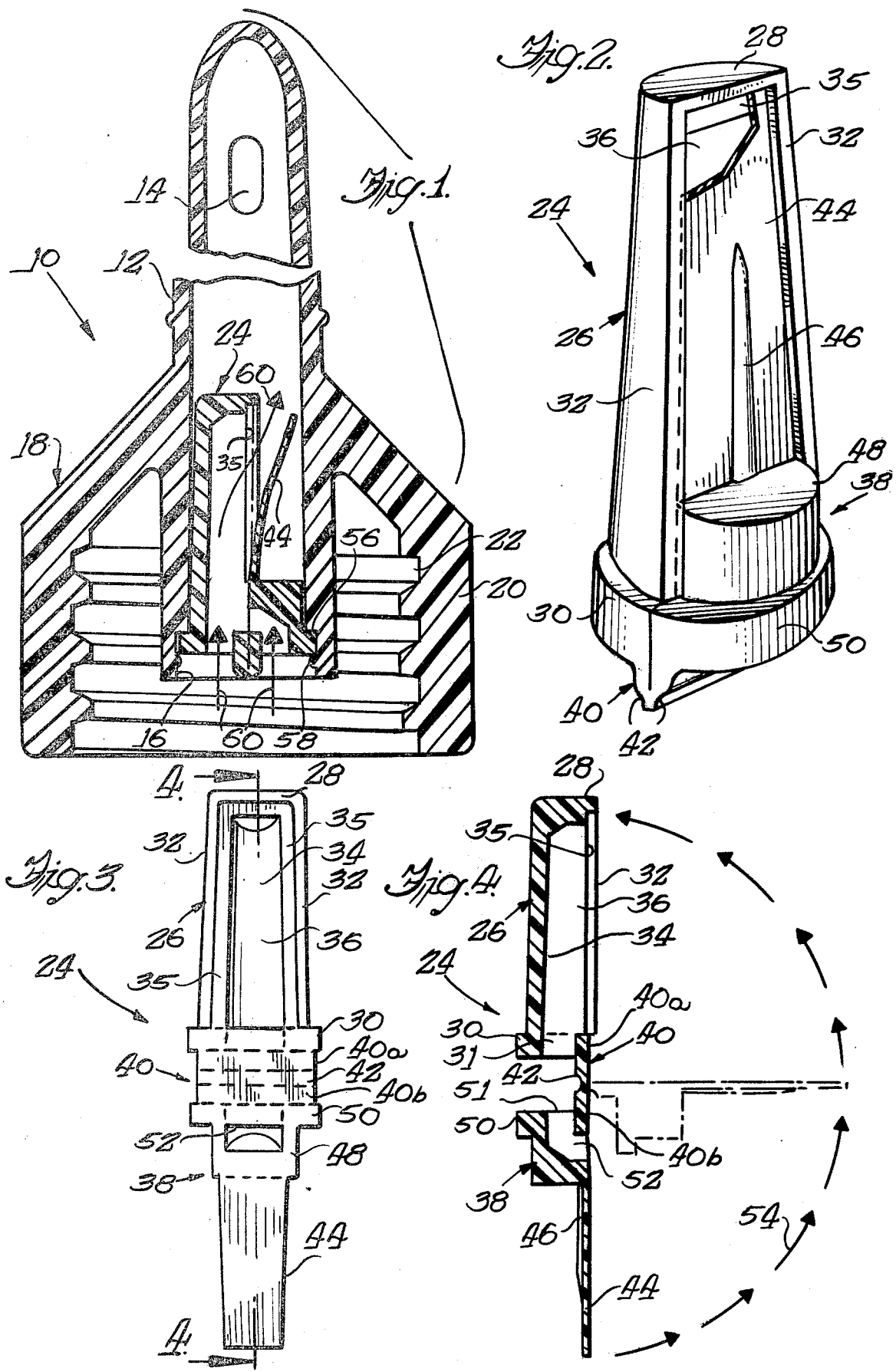

ONE-PIECE CHECK VALVE FOR USE IN A FLUID DISPENSER

BACKGROUND OF THE INVENTION

The present invention related generally to an assembly of a fluid applicator and a check valve, and more particularly to a novel, one-piece molded check valve adapted for use with said applicator.

In many applications, it is desirable to provide a simple, and relatively economical, yet reliable valve for controlling the direction of fluid flow in a fluid carrying member, such as in a disposable applicator tip used in the application of enemas. Moreover, in this type of application, the disposable tip is assembled to a reusable syringe, and it is desirable to prevent the back-flow of fluid therethrough so that the syringe itself, or any fluid remaining therein will not become contaminated.

More specifically, concerning the above-mentioned example, a disposable enema applicator tip generally comprises an elongate tube-like portion having a fluid outlet port at one end thereof and a fluid inlet port at the opposite end thereof. Connecting means are provided such as an outwardly extending rim about the inlet port of the tube-like portion formed with internal threads to engage complimentary external threads on a flexible or elastomeric bottle, syringe, or the like holding a supply of fluid for injection through the disposable applicator tip. In such an application, it is desirable to have the check valve adjacent the inlet of the tube-like portion for restricting the direction of flow therethrough, and precluding contaminated fluid from entering the syringe. More particularly, it is desirable to have a valve so arranged and constructed as to be responsive to the application of pressure at the inlet, as for example, upon squeezing the elastomeric container or syringe, to allow the passage of fluid through the tube-like portion to the outlet port thereof. Such a valve must also be responsive to absence of said applied pressure or to back pressure created upon release thereof, for positively closing the valve and preventing any backflow. Thus, the relatively inexpensive applicator tip and valve assembly may be disposed of after use, while the more expensive elastomeric fluid container or syringe remains reusable.

Accordingly, it is a general object of this invention to provide an improved disposable check valve for a fluid carrying device such as a disposable applicator tip or the like, for preventing any backflow of fluid therethrough.

A more specific object of this invention is to provide a one-piece molded disposable check valve, in accordance with the foregoing object, which is relatively simple and inexpensive to manufacture, and yet highly reliable in operation.

Briefly, a valve according to the present invention comprises a first portion, which includes a flexible reed member, and a second portion including a valve seat. A flexible, integral hinge joins the respective portions to provide a one-piece valve. Said hinge means enable the respective portions to be folded over with the reed member engaging the valve seat to close a valve chamber, thus to define a one-piece valve structure, insertable into a disposable applicator tip or the like. Inlet means may be included in one or both portions to define a valve inlet into the valve chamber provided when the portions are folded together and inserted in the applicator tip.

Other objects, features and advantages of the present invention will become apparent from the following description of the illustrated embodiment and the accompanying drawings. In this regard, it should be noted that a preferred form of the present invention will be discussed and illustrated; as such, said discussion and illustration is not intended to define the limits of the invention. It is contemplated that those skilled in the art and possessed of the present disclosure, may device various alternate structures or constructions, or devise modifications, which fall within the spirit and scope of the invention as defined by the appended claims.

BRIEF DESCRIPTION OF THE DRAWINGS

In the drawings, in which like reference numerals are used throughout to designate like elements and components:

FIG. 1 is a cross-sectional view, partially cut away, of a disposable applicator tip including a check valve, constructed in accordance with this invention;

FIG. 2 is a prespective view, somewhat enlarged, and partially cut away, of the valve of FIG. 1;

FIG. 3 is a front elevational view of the valve of FIG. 2, in its unassembled pre-folded form; and FIG. 4 is a sectional view, taken generally along the line 4—4 of FIG. 3, and illustrating in phantom the assembly of the valve portions.

DESCRIPTION OF THE ILLUSTRATED EMBODIMENT

While it is not desired to limit the present invention to a specific use or application, the following description is facilitated by addressing the problem of providing a check valve for controlling the flow of fluid in a disposable applicator tip, such as employed with an enema syringe (not shown).

Referring to the drawings, FIG. 1 illustrates a disposable applicator tip 10, suitable for use, for example, as an enema applicator tip, in conjunction with a flexible or elastomeric syringe (not shown), for supplying a suitable fluid thereto. The applicator tip 10 generally includes an elongate tube-like section 12, a central portion of which has been broken away to facilitate the illustration of FIG. 1. The tube-like portion 12 includes at least one fluid exit port 14 formed in one end thereof and a fluid inlet port 16 formed at an opposite end thereof. In the illustrated embodiment, a connecting portion or sleeve 18 is formed integral with the tube-like member 12 toward the end thereof including the fluid inlet port 16, for connecting the applicator tip 10 with a suitable syringe or the like (not shown). The connecting portion 18 generally comprises a downwardly depending annular flange 20 formed outwardly of the tube-like portion 12 in surrounding relationship to the fluid inlet port 16 thereof, and an inwardly formed thread 22. The thread 22 is adapted for engaging a complimentary thread, formed outwardly of a neck or outlet portion of a syringe or fluid supply bottle, as described above. Preferably, the fluid supply device or syringe includes an elastomeric or flexible container adapted to supply fluid through the applicator tip 10, as for example, by squeezing the container to apply pressure to the fluid, to creat a flow of fluid from the inlet port 16 through the tube-like member 12 to the outlet port 14 thereof.

A valve 24, constructed in accordance with the present invention, is associated with the applicator tip 10, being mounted in the tube-like portion 12 thereof and adjacent the fluid inlet port 16. The valve 24, as will become apparent, permits flow only in one direction, while positively precluding flow in the opposite direction.

Attention is now directed to FIGS. 1-4 inclusive for a more detailed description of the structure of valve 24.

The valve 24 includes a first or valve seat portion designated generally 26 which is shaped generally as a longitudinal half-section of a frustrum of a right cone having a relatively gentle slope, and being closed by an end wall 28 at the smaller diameter end thereof. A flange or shoulder portion 30 is formed about the outer circumference at the larger diameter end of the first or valve seat portion 26 and said flange 30 generally describes a longitudinal half-section of an annulus. The valve seat portion 26 further includes side wall portions 32 and an inner or bottom wall portion 34, which cooperates with said end wall 28 and end portion 30 to define an opened fluid chamber or opening 36. About the upper, opened edge of the chamber 36 there is provided a ledge or seat 35, defined partially by end wall 28, side walls 32 and shoulder portion 30. The ledge or seat 35 is adapted to receive the second or reed portion 38, to be described. As an additional matter, a port 31 is formed in the shoulder portion 30 to provide an inlet to said chamber 36.

The adjacent, second or reed portion 38 is joined to the first or valve seat portion 26 by an intermediate portion designated generally 40, and comprising an integral flexible hinge section 42, and a pair of generally flat, rectangular segments 40a and 40b separated by a transverse groove or valley 42. The groove or hinge 42 is of generally decreased thickness, which permits the intermediate section 40 to flex, without fracture, as will be described.

The reed portion 38 includes a relatively thin reed or flapper member 44 which is generally dimensioned to conform with the valve seat 35 defined by the side walls 32 and end walls 28 of the valve seat portion 26. The reed member 44 is initially formed with one face thereof generally co-planar with the flat face of the intermediate or hinge portion 40, and the flat faces of the flange portion 30 and seat 35 of the valve seat portion 26. A ridge or rib member 46 of somewhat increased thickness may be formed on the opposite face of the reed member 44 to provide a flexibility pattern which increases in a direction toward the free end of the member 44.

In addition, the second or reed portion 38 includes a base portion 48 which generally comprises a longitudinal half-section of a right cylinder and is disposed adjacent the intermediate section 40. The base portion 48 is generally complimentary to the shoulder portion 30, and included a radial flange 50 of increased diameter, similar to the flange 30. A port 52, including a opening 51, may be formed in the base portion 48 to provide a second inlet to the chamber 36, when the respective first and second portions are assembled.

Attention is now directed to the assembly of the valve 24, and mounting thereof in the tip 10. In this regard, the respective first and second portions 26 and 38 are adapted to be folded about the hinge 42 of the intermediate portion 40, as indicated in FIG. 4 by arrows 54 and the phantom outline of portion 38. This folding of the reed portion 38 toward the valve seat portion 26 results in the valve 24 assuming the form illustrated in FIG. 2, which is suitable for assembly and use with the applicator tip of FIG. 1 as illustrated therein. It will be noted, with respect to FIG. 2, that the flapper or reed member 44 and the base portion 48 of the reed portion 38 are dimensioned so as to abut the ledge or seat 35, and thus, are partially received within the chamber 36 of the valve seat portion 26. Also, the respective sections 40a and 40b are also engaged. Thus, the chamber 36 is, in effect closed by said second portion 38, as best seen in FIG. 2. Further, the shoulder of flange portions 30 and 50 cooperate to form a unified, generally annular shoulder or flange completely surrounding the lower portion of the valve 24.

As best seen in FIG. 1, once the respective first and second portions 26 and 36 are folded over and engaged in superposed relation as shown in FIG. 2, the valve 24 may readily be inserted into the applicator tip 10. In this regard, the tube-like portion 12 on the applicator tip 10, includes a step or aboutment shoulder 56 formed somewhat below the inlet 16 thereof. In addition inwardly extending projections or protuberances 58 are formed above the abutment shoulder 56 and spaced therefrom by a width substantially equal to the thickness of the shoulders 30 and 50 of the valve 24. Thus, the shoulder assembly on the valve 24 may be snapped past said projections 58, with said projections, and the abutment shoulder 56 maintaining the valve 24 in position, with the respective portions 26 and 28 thereof, in folded, superposed engagement.

It will be appreciated that the valve 24, as thus assembled, will restrict and control the flow of fluid through the applicator tip 10, limiting same to a path or direction as indicated by the arrows 60. More specifically, due to the relatively thin, flexible nature of the flapper or reed 44, and assuming squeezing of the syringe to which the tip 10 is attached, the increased fluid pressure will unseat the reed 44 from the ledge or seat 35, as shown in solid outline in FIG. 1. This corresponds to a valve open position for the valve 24, and allows fluid to flow out of the tip 10 via port 14. However, due to the relatively resilient nature of the reed 44 and the ridge 46 thereof, as well as the engagement of the base 48 with the valve seat, the reed 44 tends to return to the position shown in dotted line in FIG. 1, to seat on the valve seat 35. Thus, if the syringe is released or upon a back-flow of fluid into the tip 10 from opening 14 (i.e., flow in an opposite direction of the arrows 60), both said resilient nature of the reed 44 and the back pressure thus created will seal the reed 44 and ledge 35 to preclude any re-entry of fluid into valve 24 and from there into the syringe to which tip 10 is attached.

Thus, there has been shown and described herein a one-piece reed or flapper-type check valve, adapted for use in regulating the direction of fluid flow in a device such as a fluid applicator tip. The valve while simple and economical to fabricate, is effective, and facilitates the provision of an overall assembly with the tip, that can be disposed of after a single use, without the need for sterilizing or discarding the syringe. While a preferred embodiment of the invention has been shown and described herein, various changes and modifications may occur to those skilled in the art, and will be understood as forming a part of the present invention insofar as these changes and modifications fall within the spirit and scope of the invention, as defined by the appended claims.

The invention is claimed as follows:

1. A one-piece molded check valve for use in a fluid applicator tip, or the like, comprising a first portion having an open chamber with a seat about the open end thereof, and a fluid inlet port opening to said chamber, a second portion including a flexible reed member, and an integral flexible hinge section joining said first and second portions, and enabling said portions to be folded over and engaged in superposed relation, with said second portion overlying said seat to close said chamber provided by said first portion, said second portion further including an enlarged section, adjacent said reed member, with port means formed in said enlarged section and leading into said chamber when said portions are engaged in superposed relation to provide an additional inlet port for said chamber with said flexible reed member being displaceable under fluid flow from said inlet ports through said chamber to permit fluid to pass out of said chamber, with fluid flow in the opposite direction forcing said reed member into engagement with said seat to prevent flow through said chamber in said opposite direction.

2. A valve according to claim 1 wherein said seat on said first portion includes shoulder means disposed below the upper edge surface of said first portion, such that said reed member is partially received within said first portion and engaged with said shoulder upon engagement of said first and second portions.

3. A one-piece molded check valve for use in a fluid dispenser, or the like, permitting fluid flow in a single first direction, while precluding fluid flow in an opposite direction through said valve, said valve comprising a first portion defining an open chamber with a valve seat about the open portion thereof, said first portion having a shoulder disposed below the upper edge of said open portion, said shoulder providing said valve seat, and having a first fluid inlet port means opening into said chamber; a second portion joined to said first portion by an integral, flexible hinge section enabling said first and second portions to be folded over and engaged in superposed relation, said second portion including a base section, second inlet port means extending through said base section and opening into said chamber when said portions are engaged in said superposed relation, and a flexible reed member extending from said base section, such that upon said portions being folded over and engaged in said superposed relation, said base section and said reed member will overlie said seat to close said chamber provided by said first portion, with said reed member being displaceable by fluid pressure to permit fluid to pass from said inlet port means through said chamber and out of said valve in said first direction, with fluid flow through said valve in said opposite direction being precluded by said reed member which will be biased against said seat to preclude fluid flow through said chamber in said opposite direction.

4. A valve according to claim 3 wherein said first and second portions include enlarged flange segments extending perpendicular to the axis of said valve, and adapted to facilitate mounting and retention of said valve in a fluid dispenser, or the like.

5. A fluid applicator tip comprising an elongate tube-like portion having a fluid exit port at one end thereof, a fluid inlet port at an opposite end thereof, means for connecting said tip to complimentary fluid supply means, and a one piece valve means disposed in said tube-like portion intermediate said inlet and exit ports for restricting the flow of fluid therein to a desired first direction from said inlet port to said exit port while precluding fluid flow in the opposite direction, said valve comprising a first portion defining an open chamber with a seat about the open portion thereof, and having fluid inlet port means opening into said chamber; a second portion joined to said first portion by an integral, flexible hinge section enabling said first and second portions to be folded over and engaged in superposed relation, said second portion including a base section, a second inlet port means extending through said base section and opening into said chamber when said portions are engaged in said superposed relation, and a flexible reed member extending from said base section, such that upon said portions being folded over and engaged in said superposed relation, said base section and said reed member will overlie said seat to close said chamber provided by said first portion, with said reed member being displaceable by fluid pressure to permit fluid to pass from said inlet port means through said chamber and out of said valve in said first direction, with fluid flow through said valve said opposite direction being precluded by said reed member which will be biased against said seat to preclude fluid flow through said chamber in said opposite direction.

6. An applicator tip according to claim 5, wherein said tube-like portion and said valve means include cooperating retaining means for retaining said valve means therein adjacent said fluid inlet port.

7. An applicator tip according to claim 5, wherein said first portion including said chamber and said valve seat includes a shoulder disposed below the upper edges thereof, said shoulder providing said valve seat such that when said reed member is engaged therewith said reed member is partially received within said first portion.

* * * * *